United States Patent
Hsiao et al.

(10) Patent No.: US 11,096,977 B2
(45) Date of Patent: Aug. 24, 2021

(54) **DEVELOPMENT OF A STANDARDIZED AND EFFECT-OPTIMIZED HERBAL EXTRACT OF *WEDELIA CHINENSIS* AND ITS USE FOR TREATING DISEASE**

(71) Applicant: Academia Sinica, Taipei (TW)

(72) Inventors: Pei-wen Hsiao, Taipei (TW);
Chin-Hsien Tsai, Taipei (TW);
Shih-Chuan Hsieh, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 16/800,178

(22) Filed: Feb. 25, 2020

(65) Prior Publication Data

US 2020/0188463 A1 Jun. 18, 2020

Related U.S. Application Data

(62) Division of application No. 15/552,103, filed as application No. PCT/US2016/020604 on Mar. 3, 2016, now Pat. No. 10,603,346.

(60) Provisional application No. 62/128,081, filed on Mar. 4, 2015.

(51) Int. Cl.
*A61K 36/00* (2006.01)
*A61K 36/28* (2006.01)

(52) U.S. Cl.
CPC .......... *A61K 36/28* (2013.01); *A61K 2236/00* (2013.01)

(58) Field of Classification Search
None
See application file for complete search history.

(56) References Cited

FOREIGN PATENT DOCUMENTS

| CN | 103565872 A | 2/2014 |
|---|---|---|
| CN | 104230697 A | 12/2014 |

OTHER PUBLICATIONS

Lin et al "Compounds from *Wedelia chinensis* Synergistically Suppress Androgen Activity and Growth in Prostate Cancer Cells" Carcinogenesis vol. 28, pp. 2521-2529, 2007.
Tsai et al "Development of a Standardized and Effect-Optimized Herbal Extract of *Wedelia chinensis* for Prostate Cancer" Phytomedicine vol. 22, pp. 406-414, 2015.
Tsai et al "Herbal Extract of *Wedelia chinensis* Attenuates Androgen Receptor Activity and Orthotopic Growth of Prostate Cancer in Nude Mice" Clinical Cancer Research vol. 15, pp. 5435-5444, 2009.
Verma et al "Wound Healing Activity of *Wedelia chinensis* Leaves" Pharmacology Online vol. 2, pp. 139-145, 2008.

*Primary Examiner* — Qiuwen Mi
(74) *Attorney, Agent, or Firm* — Cesari & McKenna, LLP

(57) ABSTRACT

A composition including a standardized *Wedelia chinensis* extract and a method of treating an androgen-stimulated disorder with such a composition. Also provided are a method for qualifying a standardized preparation of a *Wedelia chinensis* extract for treating an androgen-stimulated disorder and a method for treating said disorder with a thus qualified preparation.

11 Claims, 4 Drawing Sheets

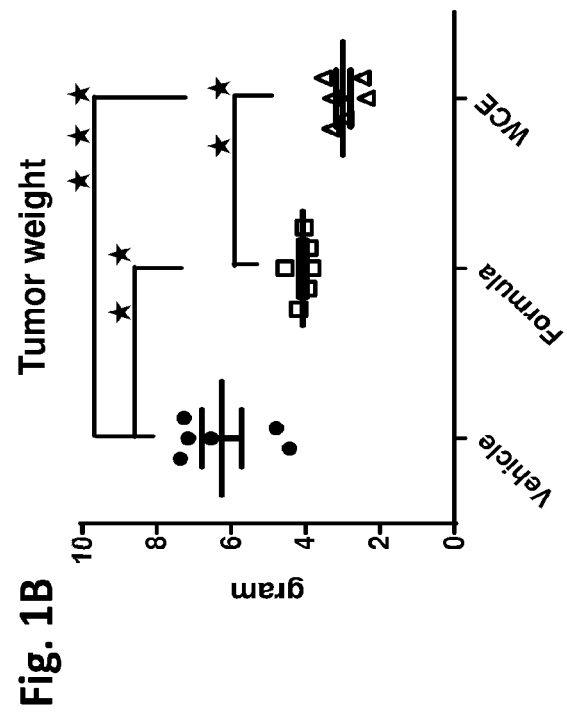
Fig. 1B
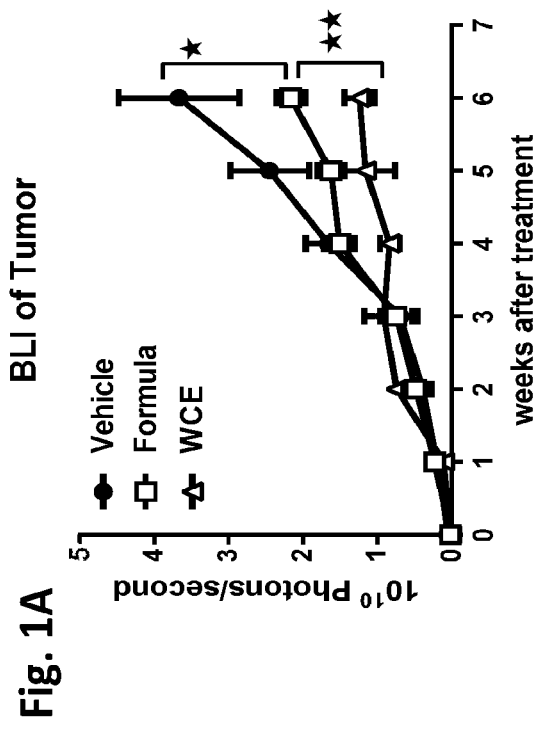
Fig. 1A
Fig. 1C

DEVELOPMENT OF A STANDARDIZED AND EFFECT-OPTIMIZED HERBAL EXTRACT OF *WEDELIA CHINENSIS* AND ITS USE FOR TREATING DISEASE

CROSS REFERENCE TO RELATED APPLICATIONS

This application is a Division of application Ser. No. 15/552,103 filed on Aug. 18, 2017, which is the National Stage of International Application No. PCT/US2016/020604, filed on Mar. 3, 2016, which claims priority to Provisional Application No. 62/128,081, filed on Mar. 4, 2015. The contents of these applications are hereby incorporated by reference in their entirety.

BACKGROUND

Field

This application relates to herbal medicines extracted from *Wedelia chinensis* as a complementary or alternative treatment for disease.

Background Information

Plant secondary metabolites display a myriad of chemical structures with accompanying activities that have pharmaceutical potential. Plants used in traditional medicinal systems provide a rational and obvious source of candidates for targeted identification of lead substances with novel structures, combinations, and mechanisms of action. Plant extracts also have the added advantage that, as drugs, their safety and efficacy profiles are well established through historical use or long-term human experience. For example, *Wedelia chinensis* (Osbeck) Merr., belonging to the Asteraceae (Compositae) family, is a medicinal plant with great pharmaceutical potential that has been traditionally used for treating common inflammatory diseases.

Due to the inherent complexity of the chemical composition of herbal extracts, conventional quality control techniques are insufficient for assessing the batch-to-batch consistency of herbal drugs. For example, genetic variability, physiological, and environmental variables, such as photoperiod, climate, and nutrient conditions in the soil, affects the secondary metabolite production in plants and biochemical profiles of the raw material. The content of secondary metabolites including active compounds are also dependent on harvesting time, temperature, post-harvest storage, drying, extraction and processing of the final product.

The need exists to develop standardized methods for preparing herbal extracts and techniques for assessing the batch-to-batch variability of the extracts in order to prepare safe drugs having maximized and standardized efficacy.

SUMMARY

To meet the need mentioned above, a method is disclosed for preparing a standardized *Wedelia chinensis* extract. The method includes the steps of providing an ethanolic extract of *Wedelia chinensis*, acid-hydrolyzing the ethanolic extract, neutralizing the acid-treated ethanolic extract, applying the neutralized acid-treated ethanolic extract to a reverse phase column, eluting and collecting fractions from the reverse phase column, assaying in vitro the collected fractions for anti-androgen receptor activity, and combining fractions having high anti-androgen receptor activity.

A composition is also provided that contains a standardized *Wedelia chinensis* extract prepared by the above method.

Further provided herein is a method for qualifying a standardized preparation of a *Wedelia chinensis* extract for treating an androgen-stimulated disorder.

The method includes the steps of obtaining a plurality of standardized preparations of a *Wedelia chinensis* extract, analyzing each standardized preparation to quantify its most abundant compounds, assaying each standardized preparation for anti-androgen receptor activity in vitro, and correlating the quantities of the most abundant compounds in each standardized preparation with the corresponding in vitro anti-androgen receptor activity to determine a threshold activity level. A standardized preparation of the *Wedelia chinensis* extract is qualified for treating an androgen-stimulated disorder if its anti-androgen receptor activity is higher than the determined threshold activity level.

Additionally, disclosed is a method for treating an androgen-stimulated disorder. The method includes the steps of identifying a subject in need of treatment for an androgen-stimulated disorder, and administering to the subject a composition containing a standardized preparation of a *Wedelia chinensis* extract that has been produced by the method set forth, supra.

Also disclosed is the use of a qualified standardized *Wedelia chinensis* extract for treating an androgen-stimulated disorder.

The details of one or more embodiments of the invention are set forth in the description and in the examples below. Other features, objects, and advantages of the invention will be apparent from the detailed description, the drawings, and also from the claims. All references cited herein are hereby incorporated by reference in their entirety.

BRIEF DESCRIPTION OF THE DRAWINGS

The invention description below refers to the accompanying drawings, of which:

FIG. 1A is a plot of bioluminescence versus time after the indicated treatment: vehicle=control, WCE=standardized *Wedelia chinensis* extract, formula=mixture of purified active compounds wedelolactone, luteolin, and apigenin;

FIG. 1B is a dot plot of tumor mass for each treatment;

FIG. 1C is a plot of body weight versus time;

DETAILED DESCRIPTION

Figure 2A:
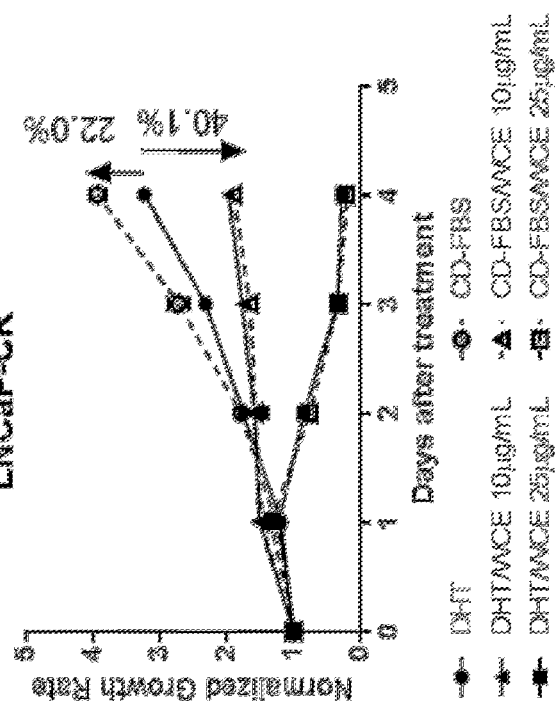
FIG. 2A is a plot of normalized growth rate versus time for LNCaP cells treated with dihydrotestosterone (DHT), WCE, charcoal-dextran stripped fetal bovine serum (CD-FBS), and combinations of DHT/WCE and CD-FBS/WCE.

As mentioned above, a method for preparing a standardized *Wedelia chinensis* extract is disclosed in which an acid-hydrolyzed ethanolic extract of *Wedelia chinensis* is neutralized and then fractionated on a reverse phase column.

The reverse phase column can be a C18 column. The column can be equilibrated with, e.g., a mobile phase of 80% $H_2O$:20% ethanol to wash out unbound material. Fractions can be eluted with an $H_2O$:ethanol gradient. The gradient can be from 80% $H_2O$:20% ethanol by volume to 50% $H_2O$:50% ethanol by volume. In a particular aspect, the gradient is a linear gradient. Fractions can be identified by ultraviolet light absorption. The ultraviolet light can be 320 nm and 210 nm. In an embodiment, six fractions are eluted and collected. Alternatively, the method can be used to make a standardized extract from *Eclipta prostrata* and from *Eclipta alba*.

The method also includes a step of assaying in vitro the anti-androgen receptor activity in the fractions. In one aspect, the anti-androgen receptor activity can be determined by a prostate-specific antigen promoter/reporter assay. Fractions having high anti-androgen receptor activity can be combined to form the standardized *Wedelia chinensis* extract. Preferably, the two fractions having the highest anti-androgen receptor activity are combined to form the standardized *Wedelia chinensis* extract. A standardized extract from *Eclipta prostrata* and from *Eclipta alba* can be made using the same method.

Also mentioned above is a method for qualifying the standardized *Wedelia chinensis* extract. The method relies on correlating the amounts of the most abundant compounds in the standardized *Wedelia chinensis* extract with its in vitro anti-androgen receptor activity. The in vitro anti-androgen receptor activity can be determined, e.g., by a prostate-specific antigen promoter/reporter assay. Further, the amounts of abundant compounds can be measured quantitatively by, for example, LC-MS-MS.

The correlation is preferably determined by principle component analysis followed by orthogonal signal correction partial least squares discriminant analysis. The correlation allows for grouping of individual extracts such that a threshold activity level can be determined. Standardized *Wedelia chinensis* extracts having an anti-androgen receptor activity above the threshold activity level are considered to be qualified.

A qualified standardized *Wedelia chinensis* extract is effective in vivo for treating an androgen-stimulated disease. An androgen-stimulated disease is any abnormal health condition that is caused by or worsened by androgen receptor activity, e.g., prostate cancer, benign prostate hypertrophy, breast cancer, male alopecia, *Propionibacterium acnes* infection, polycystic ovarian syndrome, autosomal dominant polycystic kidney disease, and hyperandrogenism. In a particular aspect, the prostate cancer is castration-resistant prostate cancer.

In this connection, a method for treating an androgen-stimulated disease by administering a standardized *Wedelia chinensis* extract is provided. Preferably, the standardized *Wedelia chinensis* extract has been qualified by the method described above. In one aspect, the qualified *Wedelia chinensis* extract can be combined with pharmaceutically acceptable excipients.

As mentioned above, provided is the use of a qualified *Wedelia chinensis* extract for treating an androgen-stimulated disorder. The androgen-stimulated disorder can be prostate cancer, benign prostate hypertrophy, breast cancer, male alopecia, *Propionibacterium acnes* infection, polycystic ovarian syndrome, autosomal dominant polycystic kidney disease, and hyperandrogenism. In a particular aspect, the qualified *Wedelia chinensis* extract is used for treating castration-resistant prostate cancer.

The following specific examples are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Example 1: Preparation of a Standardized *Wedelia chinensis* Extract

*Wedelia chinensis* plants were harvested at a single farm (Erchong Floodway, New Taipei City, Taiwan) in different months. *W. chinensis* can also be grown and harvested in other areas of Taiwan, e.g., Tainan City, with similar results. The aerial parts of the plants were air-dried, ground, and extracted with 95% ethanol. After condensing, the extract was acid-hydrolyzed at 80° C. with HCl at pH 2.0 for 1 h to enhance the aglycone flavonoid content, then neutralized with NaOH and applied to a flash LC system (IsoleraOne, Biotage, Uppsala, Sweden) using a C18 column (SNAP400KP-C18-HS Column, Biotage). After applying the acid-hydrolyzed/neutralized extract to the column, the column was equilibrated with 80% $H_2O$:20% ethanol by volume as a mobile phase to wash out an initial inactive fraction, termed "fraction W0." A linear ethanol/$H_2O$ gradient (80% $H_2O$:20% ethanol by volume to 50% $H_2O$:50% ethanol by volume) was used to separate the extract into 6 eluted fractions, i.e., fractions W1-W6. The eluted fractions were identified by ultraviolet absorption at 320 nm and 210 nm. Finally, 100% ethanol was applied as the mobile phase to wash out any remaining material from the column. This material was collected as fraction W7.

The anti-androgen receptor activity of each fraction was determined in vitro by performing prostate-specific antigen promoter-luciferase reporter gene (PSA-LUC) assays using 103E clones of 22Rv1 cell origin as described previously See Lin et al., 2007, Carcinogenesis 28:2521-2529 ("Lin"). An exemplary result is shown in Table 1 below.

TABLE 1

Anti-androgen receptor activity of *Wedelia chinensis* fractions determined by PSA-LUC assay

| | conc. tested | | | |
|---|---|---|---|---|
| Fraction | 0.1 µg/ml | 1 µg/ml | 5 µg/ml | 10 µg/ml |
| W0 | −5.53415[a] | −1.05249 | −7.05624 | −3.42755 |
| W1 | 6.685838 | 23.10923 | 61.18957 | 72.1662 |
| W2 | 4.038085 | 25.87721 | 42.66556 | 70.59276 |
| W3 | −3.0371 | 20.48604 | 37.46817 | 51.92206 |
| W4 | 30.55909 | 63.34848 | 78.58248 | 80.68148 |
| W5 | 13.6625 | 43.33377 | 57.34047 | 85.52312 |
| W6 | 7.406954 | 4.19102 | 21.3737 | 43.48958 |
| W7 | 6.685279 | 4.314428 | 13.45211 | 23.94393 |

[a]values are expressed as percentage inhibition of control PSA-LUC activity

The results demonstrated that fractions W4 and W5 had the highest anti-androgen receptor activity. See bold values in Table 1 above. Fractions W4 and W5 were combined to form a standardized extract, termed Wedelia chinensis extract ("WCE"). On average, the yields of W4 and W5 were 0.25% and 0.11% (weight %) from the dry plants, and 2.25% and 0.97% (weight %) from the crude extract, respectively. Fractions W4 and W5, together, constitute 0.35% (weight %) from dry plant and 3.22% (weight %) from crude extract, respectively. The WCE was dried, frozen, and stored at −80° C. for later use.

Example 2: Characterization of a Standardized Wedelia chinensis Extract

Batches of standardized Wedelia chinensis extracts (WCE) were analyzed from plants harvested in different months to determine anti-androgen receptor activity as well as the amounts of major compounds in the extracts. The proportion by mass of individual compounds in WCE was determined by LC/MS/MS. The results are shown in Table 2 below.

TABLE 2

Analysis of 15 batches of WCE

| Batch | Lut[a] | Wed[a] | Api[a] | Lut + Wed + Api[a] | 3D-4CQA[a] | Peak 5[a] | Peak 6[a] | Peak 7[a] | Total[a] | $IC_{50}$ (ng/ml)[b] |
|---|---|---|---|---|---|---|---|---|---|---|
| 1 | 27.96 | 0.17 | 13.39 | 41.51 | 6.66 | 5.98 | 1.23 | 2.67 | 58.04 | 1228.0 |
| 2 | 29.54 | 4.89 | 11.15 | 45.58 | 7.21 | 4.40 | 1.20 | 1.18 | 59.57 | 403.6 |
| 3 | 38.48 | 0.79 | 11.74 | 51.01 | 5.94 | 0.20 | 1.65 | 2.89 | 61.70 | 820.5 |
| *4* | *29.67* | *10.96* | *12.07* | *52.69* | *6.72* | *0.57* | *1.19* | *1.21* | *62.38* | *168.1* |
| *5* | *22.56* | *14.54* | *4.95* | *42.05* | *9.60* | *3.72* | *1.19* | *0.00* | *56.56* | *161.5* |
| 6 | 32.77 | 6.61 | 6.07 | 45.46 | 12.11 | 0.32 | 0.91 | 1.40 | 60.20 | 459.6 |
| *7* | *26.06* | *8.69* | *10.43* | *45.17* | *8.71* | *0.67* | *1.31* | *1.41* | *57.27* | *195.1* |
| *8* | *36.19* | *7.61* | *16.67* | *60.47* | *7.22* | *0.78* | *1.35* | *1.29* | *71.11* | *275.9* |
| *9* | *26.05* | *11.26* | *10.00* | *47.31* | *6.13* | *0.37* | *3.10* | *2.36* | *59.25* | *170.3* |
| *10* | *38.42* | *11.45* | *13.14* | *63.01* | *0.72* | *0.51* | *1.31* | *1.19* | *66.74* | *196.2* |
| *11* | *31.70* | *9.36* | *9.08* | *50.14* | *9.81* | *2.46* | *2.40* | *1.63* | *66.43* | *180.9* |
| 12 | 32.90 | 5.65 | 8.60 | 47.16 | 6.97 | 4.30 | 2.64 | 1.57 | 62.64 | 826.0 |
| 13 | 28.79 | 4.33 | 14.69 | 47.81 | 0.92 | 4.43 | 2.32 | 2.74 | 58.23 | 801.1 |
| 14 | 28.78 | 5.86 | 8.82 | 43.47 | 10.88 | 1.03 | 2.85 | 3.86 | 62.10 | 931.0 |
| 15 | 30.94 | 2.81 | 7.25 | 41.00 | 10.27 | 0.59 | 2.48 | 4.49 | 58.83 | 1116.0 |

[a]values expressed as percentage of total mass of WCE batch analyzed
[b]values determined from PSA-LUC assay described above in Example 1.

Chemical profiling of each WCE batch was performed by HPLC coupled with a charged aerosol detector. The results indicated that each batch had very similar chemical profiles that included wedelolactone, luteolin, and apigenin, the previously known major active components of Wedelia chinensis. See Lin.

Additional compounds in the WCE were identified and quantified by triple-quadrupole LC-MS-MS analysis. The results are shown in Table 2 above. The four next most abundant compounds after wedelolactone, luteolin, and apigenin were further characterized, including 3-O-dimethoxycinnamoyl-5-O-caffeoylquinic acid and three additional unknown compounds, designated as peaks 5, 6, and 7.

A total of 15 batches of WCE were initially studied by PSA-LUC assay to measure the potency of their biological activity expressed as $IC_{50}$ values. The results, shown above in Table 2, last column, indicated that the anti-androgen receptor activity varied among different batches of W. chinensis harvested in different months.

Example 3: Qualification of a Standardized Wedelia chinensis Extract

To correlate the variable proportion of each abundant compound with the potency of the whole WCE, a principal component analysis (PCA) of the 15 WCE batches was performed.

The locations of the WCE batches in a bi-plot diagram were distributed in two correlation circles. Orthogonal signal correction partial least squares discriminant analysis (OPLS-DA) was then employed to maximally separate the variance between the two groups observed by PCA. Among the 15 WCE batches, OPLS-DA analysis clearly separated one group with an $IC_{50} \leq 300$ ng/ml (potent batches) from the others with an $IC_{50} \geq 400$ ng/ml (non-potent batches). See bold italicized entries in Table 2 above. A batch of WCE was considered to be qualified if it had an in-vitro $IC_{50} \leq 300$ ng/ml in the PSA-luciferase assay.

The corresponding score (S-plot) of the above OPLS-DA suggested that among the seven most abundant compounds in WCE, wedelolactone contributed the most to the clustering of potent and non-potent groups. Indeed, the $IC_{50}$ values between the two groups were statistically significant. This result indicated that wedelolactone content can dominate the anti-androgen receptor activity of WCE.

Example 4: Bioavailability and Metabolism of Compounds Present in WCE

The bioavailability and metabolic rate of active compounds, i.e., wedelolactone, luteolin, and apigenin, when they are administered as WCE were compared to those values when administering the active compounds as a mixture of highly purified compounds ("formula"). Wedelolactone, luteolin, and apigenin were purified from WCE and combined to prepare the formula. In addition, minor compounds co-eluting together with wedelolactone, luteolin, and apigenin in the W4 and W5 fractions mentioned above were separated from these active compounds and designated as the "matrix fraction." As determined by PSA-LUC assay, the formula had much higher AR-inhibition activity ($IC_{50}=228.1$ ng/ml) as compared to the matrix ($IC_{50}=7435$ ng/ml). Surprisingly, the anti-AR activity of WCE ($IC_{50}$=264.9 ng/ml) was not significantly different from that of the formula, made up of purified wedelolactone, luteolin, and apigenin.

To study the effect of compounds in the matrix fraction on the in vivo absorption and metabolism of the active compounds, a pharmacokinetic study was performed by oral administration with a single dose of WCE at 100 mg/kg or an equivalent amount of formula (purified active compounds). Plasma concentrations of free active compounds and their respective conjugates to glucuronic acid and sulfate were analyzed at different dosing intervals by LC/MS/MS. In a plasma concentration time curve, free, unconjugated luteolin in WCE-treated mice remained detectable beyond 8 h after administration. By contrast, luteolin in formula-treated mice dropped below the detection limit within 8 h. In agreement, WCE-treated mice had higher extent of exposure ($AUC_{0-inf}$) and maximum concentration ($C_{max}$) of luteolin than that in formula-treated mice. Furthermore, the clearance rate (Cl/F_obs) of luteolin was 43.6% lower in WCE-treated mice than in formula-treated mice.

Regarding apigenin, there was no significant difference in extent of exposure, maximum concentration, and clearance rate between WCE-treated mice and formula-treated mice.

Turning to wedelolactone, the level of free unconjugated wedelolactone was below the detection limit of 10 nM in both WCE-treated and formula-treated mice.

Serum samples were then hydrolyzed with a mixture of β-glucuronidase and sulfatase to ascertain the kinetics of the total amounts, both unconjugated and conjugated, of the three active compounds. The results are shown in Table 3 below.

Analyses of total active compounds showed that the $AUC_{0-inf}$ for wedelolactone was 40.7% higher in WCE-treated versus formula-treated mice. See Table 3. On the other hand, the clearance rate of wedelolactone from the circulation was slower in WCE-treated mice as compared to formula-treated animals, despite the fact that the $C_{max}$ of wedelolactone was slightly decreased by administration as part of the extract. See Table 3 above.

Furthermore, in WCE-treated mice, the $AUC_{0-inf}$ and the $C_{max}$ of apigenin were increased by 108.1% and 98.1%, respectively, and the clearance rate was decreased by 54.2% compared to the formula-treated animals. See Table 3 above.

Luteolin exhibited only a slight change of metabolism when administered as part of the WCE versus as part of the formula, demonstrating an increase in $AUC_{0-inf}$ and a decrease in clearance with no change in $C_{max}$. See Table 3 above.

The data, taken together, showed that the presence of matrix compounds in WCE resulted in higher bioavailability of the major active compounds, i.e., wedelolactone, luteolin, and apigenin, by increasing their in vivo half-life as compared to a mixture of purified major compounds.

Example 5: In Vivo Anti-Tumor Activity of Standardized *Wedelia chinensis* Extract The human prostate cancer 22Rv1 cell line, which expresses the androgen receptor, responds to androgen-stimulation, but grows independently in the absence of androgen, was stably transfected with firefly luciferase luc2 of pGL4 (Promega, Madison, Wis.) driven by a hybrid EF1α/eIF4g promoter through lentivirus infection to yield 22Rv1Luc2 cells. See Hsu et al., 2012, Cell Rep. 2:568-579.

Tumors were formed in athymic nude mice (6 weeks old) at subcutaneous and orthotopic sites by implantation of 22Rv1Luc2 cells as previously described. See Tsai et al., 2009, Clin. Cancer Res. 15:5435-5444.

WCE dissolved in phosphate buffered saline with 10% (v/v) DMSO and 5% (v/v) Tween-80 (vehicle) was admin-

TABLE 3

Pharmacokinetic parameters of conjugated and unconjugated active compounds in plasma.

| | Wedelolactone | | | Apigenin | | |
|---|---|---|---|---|---|---|
| | Formula mean (±SE) | WCE mean (±SE) | p-value | Formula mean (±SE) | WCE mean (±SE) | p-value |
| Cmax (nM) | 14192 (1833) | 11631 (76.4) | <0.0001 | 3008 (138.4) | 5960 (101.0) | <0.0001 |
| Tmax (h) | 0.25 | 0.5 | | 0.25 | 0.5 | |
| $t_{1/2}$ (h) | 1.36 (0.136) | 2.16 (0.165) | 0.0094 | 4.80 (0.637) | 4.40 (0.355) | 0.1989 |
| $AUC_{0-inf}$ (nM h) | 14914 (1228) | 20987 (2059) | 0.0445 | 5367 (708) | 11169 (484) | 0.0005 |
| $MRT_{0-inf}$ (h) | 1.93 (0.259) | 3.36 (0.150) | 0.0031 | 4.43 (0.527) | 4.66 (0.342) | 0.6313 |
| Cl/F_obs (g M−1h−1) | 15.97 (1.425) | 11.44 (1.140) | 0.0474 | 66.63 (8.938) | 30.53 (1.344) | 0.0072 |

| | Luteolin | | |
|---|---|---|---|
| | Formula mean (±SE) | WCE mean (±SE) | p-value |
| Cmax (nM) | 13877 (102.4) | 13347 (3313) | 0.1775 |
| Tmax (h) | 0.25 | 0.5 | |
| $t_{1/2}$ (h) | 6.21 (0.090) | 7.61 (0.466) | 0.0256 |
| $AUC_{0-inf}$ (nM h) | 30430 (1441) | 41254 (2440) | 0.0088 |
| $MRT_{0-inf}$ (h) | 7.40 (1.465) | 9.77 (1.318) | 0.2733 |
| Cl/F_obs (g M−1h−1) | 27.24 (2575) | 20.24 (1.153) | 0.0478 | istered via gavage. WCE was administered at dosages of 2 mg/kg and 10 mg/kg for 5 weeks. A significant decrease in tumor size was observed after administering a qualified WCE ($IC_{50} \leq 300$ ng/ml) at both dosages. An unqualified WCE, having an in vitro $IC_{50}>400$ ng/ml, demonstrated tumor inhibition only at the high dose, i.e., 10 mg/kg.

Example 6: In Vivo Anti-Tumor Activity of WCE and Purified Active Compounds

WCE and formula described above in Example 4 were further analyzed in the orthotopic 22Rv1 prostate cancer model described above in Example 5. The results indicated that WCE was more effective than the formula in suppressing tumor growth when administered to tumor-bearing mice. See FIG. 1A. A similar differential effect was seen on tumor mass, with WCE demonstrating significantly less tumor weight as compared to formula. See FIG. 1B. Body weight of treated animals were similar between WCE-treated and formula-treated mice.

Example 7: Effect of WCE in an In Vitro Model of Castration-Resistant Prostate Cancer Castration-resistant prostate cancer cells were formed by orthotopically injecting into mouse prostate $2 \times 10^5$ cells of an androgen-dependent prostate cancer cell line that expresses the luciferase gene, i.e., LNCaP cells. After 4 weeks, the mice were castrated by surgical removal of the testes. During the next 10 weeks, tumors formed from the injected cells, underwent remission, and recurred in the castrated mice. The tumors were excised upon necropsy and prostate cancer cells in the tumors were cultured. These cells were termed "LNCaP-CR cells." Unlike the parental LNCaP cells, which depend upon the presence of androgen for growth, the LNCaP-CR cells are androgen-independent, as demonstrated by growth in medium free of androgens. See below.

Figure 2B:
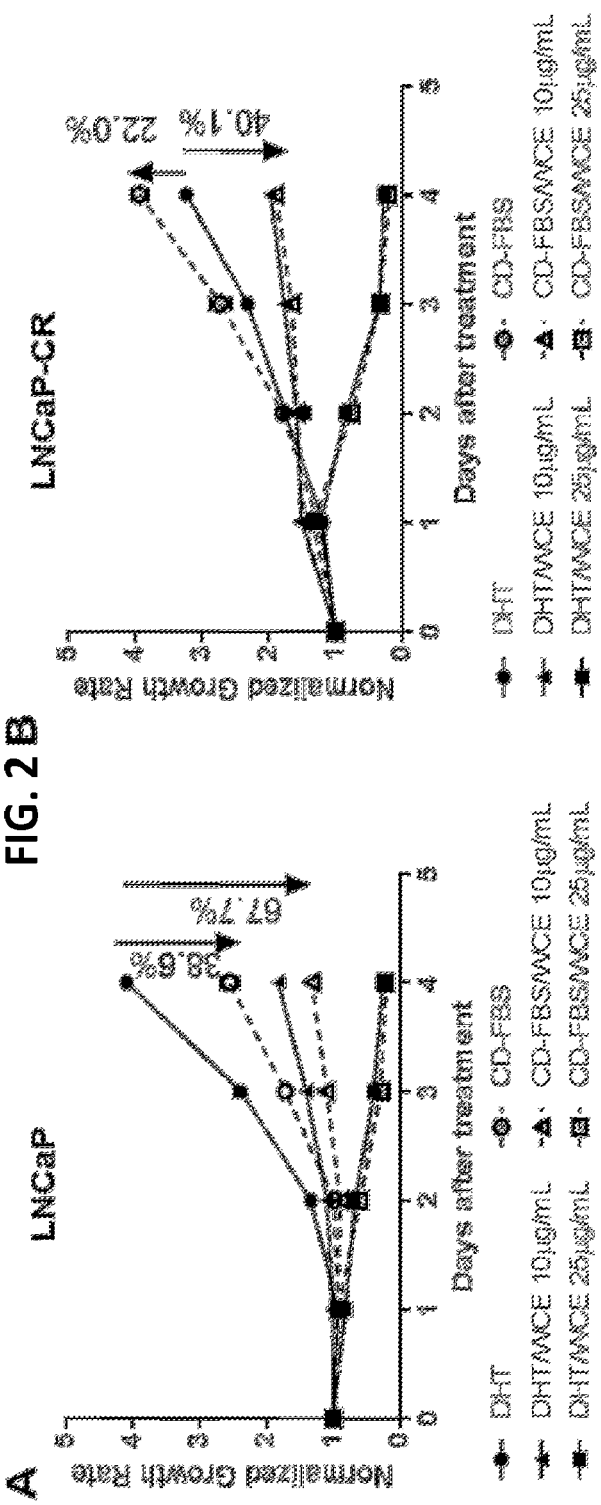
FIG. 2B is a plot of normalized growth rate versus time for LNCaP-CR cells treated with DHT, WCE, CD-FBS, and combinations of DHT/WCE and CD-FBS/WCE.

The effect of WCE on the growth of LNCaP and LNCaP-CR cells was determined. LNCaP and LNCaP-CR cells were grown in RPMI-1640 medium supplemented with Fetal Bovine Serum that was charcoal-dextran stripped (CD-FBS) to remove any androgens form the serum. Dihydrotestosterone (DHT) was added to certain cultures at $1 \times 10^{-8}$ M. WCE was added at 10 µg/ml or 25 µg/ml to certain cultures. The growth rate of treated and control cultured cells was measured over a 4 day period. The results are shown in FIGS. 2A and 2B.

Growth of the androgen-dependent LNCaP cells was 38.6% lower in cells cultured in CD-FBS versus DHT. See FIG. 2A. WCE added at 10 µg/ml also inhabited DHT-dependent growth and was also effective at reducing growth in the absence of androgen (see CD-FBS/WCE 10 µg/ml in FIG. 2A). WCE added at 25 µg/ml suppressed cell growth nearly completely. See FIG. 2A.

The effect of WCE on LNCaP-CR cells was determined as described above. The results are shown in FIG. 2B. Treatment with 10 µg/ml WCE resulted in a reduction of cell growth by at least 40% as compared to control or DHT-treated LNCaP-CR cells. Increasing the amount of WCE to 25 µg/ml resulted in little to no growth of the LNCaP-CR cells. See FIG. 2B.

Example 8: Combination of WCE and Anti-Androgen

Figure 2C:
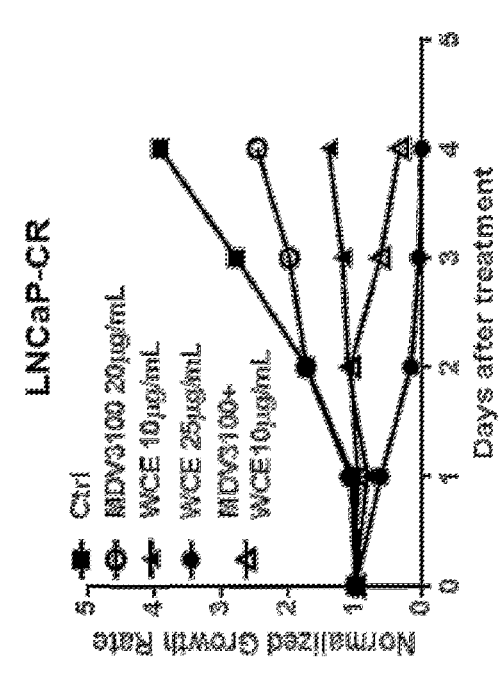
FIG. 2C is a plot of normalized growth rate versus time for LNCaP cells treated with enzalutamide (MDV3100), WCE, and combinations of MDV3100 and WCE.
Figure 2D:
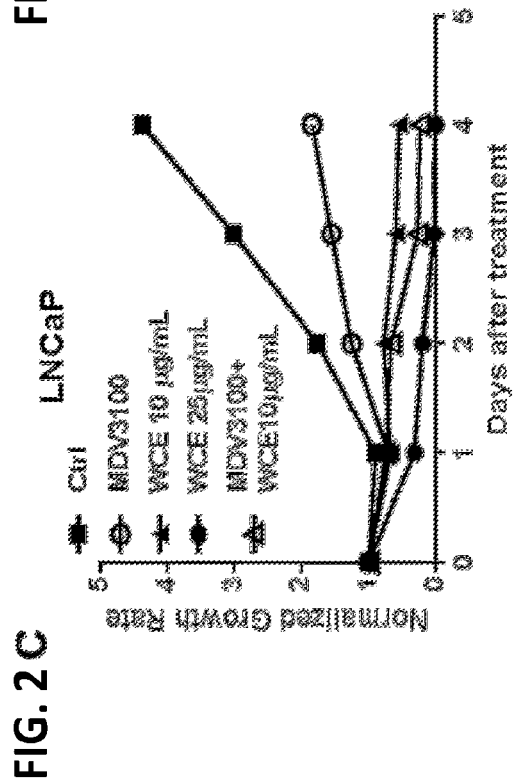
FIG. 2D is a plot of normalized growth rate versus time for LNCaP-CR cells treated with enzalutamide (MDV3100), WCE, and combinations of MDV3100 and WCE.

The combined effect of WCE and enzalutamide, an anti-androgen, was assessed in vitro. The LNCaP and LNCaP-CR cells, both described above, were (i) untreated, (ii) treated with 20 µg/ml enzalutamide, (iii) treated with 10 µg/ml WCE, (iv) treated with 25 µg/ml WCE, and (v) treated with 20 µg/ml enzalutamide plus 10 µg/ml WCE. The results are shown in FIGS. 2C and 2D.

Enzalutamide significantly inhibited the growth of androgen-dependent LNCaP cells. See FIG. 2C (enzalutamide is designated as MDV3100). As expected, treatment of the androgen-independent LNCaP-CR cells with enzalutamide resulted in significantly less growth inhibition. See FIG. 2D. WCE treatment at 10 µg/ml was much more effective at suppressing cell growth as compared to enzalutamide. WCE at 25 µg/ml effectively blocked the growth of LNCaP and LNCaP-CR cells. Importantly, the combination of 20 µg/ml enzalutamide with 10 µg/ml WCE blocked growth of both LNCaP and LNCaP-CR cells more than either treatment alone and combined use of enzalutamide and WCE at low dose enhanced the therapeutic effect of enzalutamide. See FIGS. 2C and 2D.

Example 9: WCE in Combination with Docetaxel Inhibits Growth of Androgen-Receptor Negative Prostate Cancer Cells In Vitro The effect of WCE and docetaxel on androgen receptor-negative (AR-negative) prostate cancer cell lines PC-3 and DU145 was assessed. Cultures of these cells were untreated, treated with WCE at 25 µg/ml, treated with 10 nM docetaxel, or treated with both. After 48 h, viable cell numbers were determined using CyQUANT direct cell proliferation assay. The results are shown in FIGS. 3A and 3B.

Figure 3:
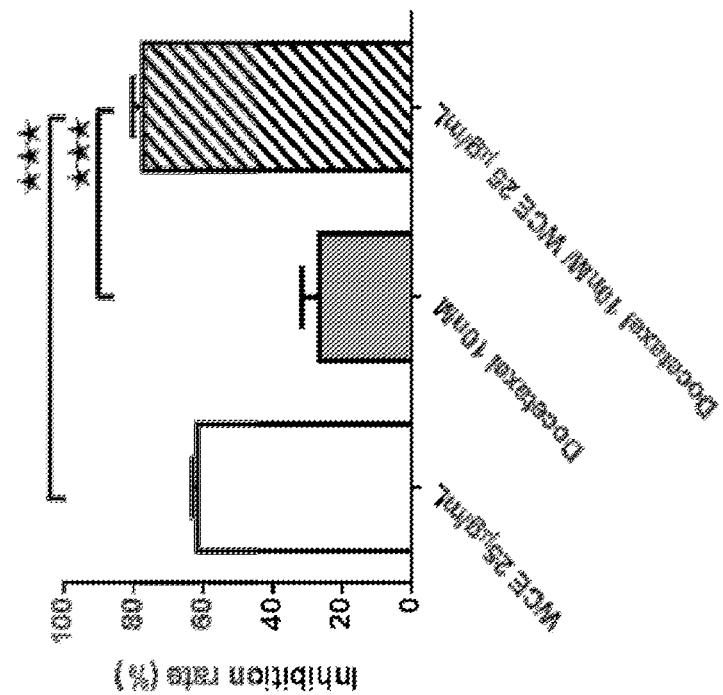
FIG. 3A is a bar graph showing the effect of WCE, docetaxel, and both on the growth of PC-3 androgen receptor negative (AR−) prostate cancer cells.
FIG. 3B is a bar graph showing the effect of WCE, docetaxel, and both on the growth of DU145 AR-prostate cancer cells.
Figure 3:
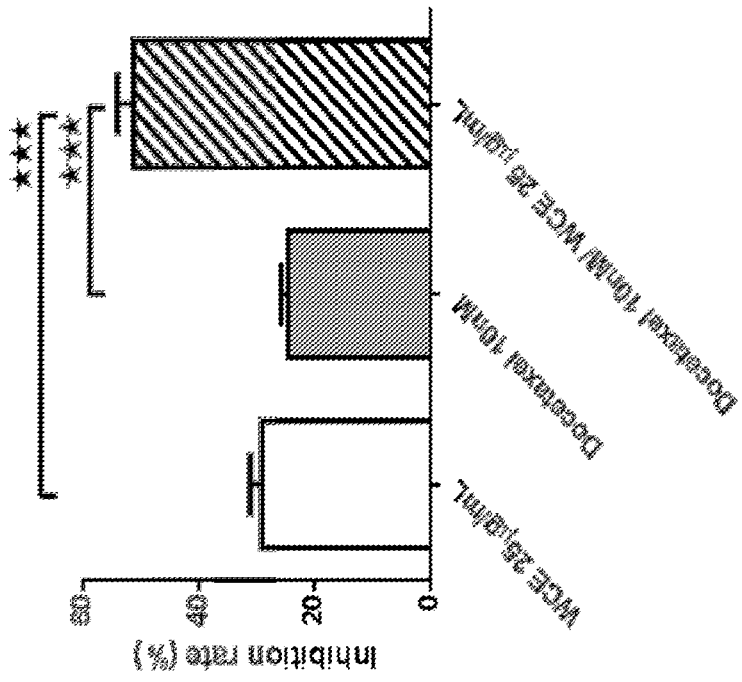

Both WCE and docetaxel inhibited growth of PC-3 cells (FIG. 3A) and DU145 cells (FIG. 3B). Combining these two treatments resulted in further inhibition of cell growth by as much as 80%. Also see FIGS. 3A and 3B.

Example 10: In Vivo Anti-Tumor Activity of WCE

The effect of WCE on tumor growth in vivo was studied in a murine model for androgen independent prostate cancer. PC-3 AR-negative prostate cancer cells carrying a luciferase reporter gene were injected into mouse prostate at $1 \times 10^5$ cells per animal One week following the injection, the mice were divided into four groups and treated for 6 weeks as follows: Group 1: control, vehicle only; Group II, a daily dose of WCE through gavage; Group III, weekly docetaxel injection into the tail vein; and Group IV, both daily WCE and weekly docetaxel. Tumor growth was measured weekly by bioluminescent imaging. Animals were also weighed weekly.

Figure 4A:
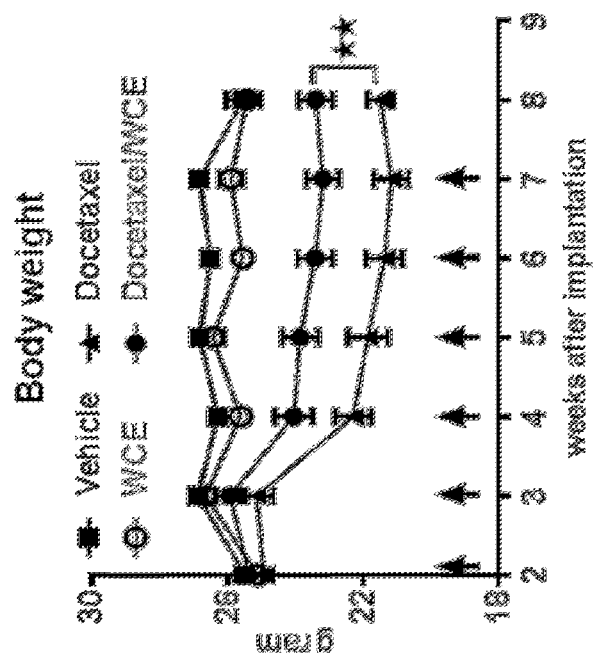
FIG. 4A is a plot of bioluminescence versus time after the indicated treatments: ctrl=control, WCE=standardized *Wedelia chinensis* extract, taxel=docetaxel.
Figure 4B:
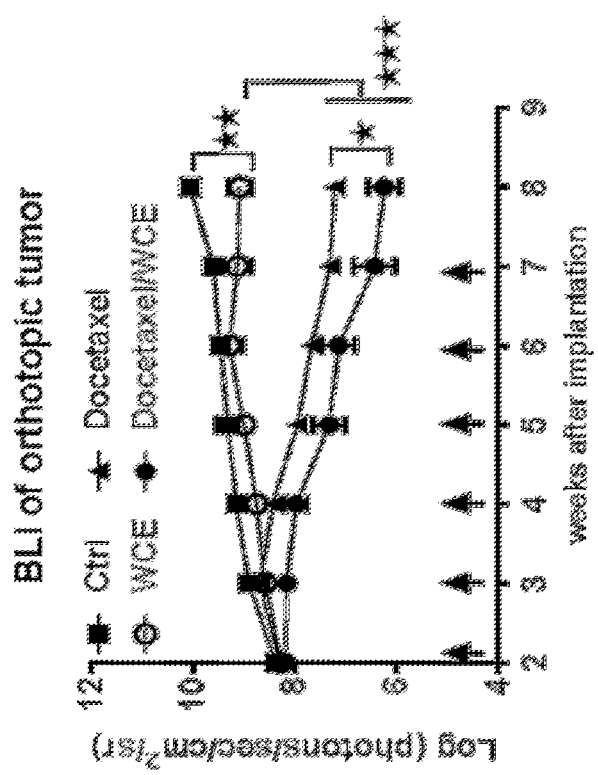
FIG. 4B is a plot of body weight versus time after the indicated treatments.

The results are shown in FIGS. 4A and 4B.

WCE was significantly more effective than docetaxel at inhibiting tumor growth in vivo. See FIG. 4A. The combination of these two treatments was the most effective for inhibiting tumor growth. Id. Turning to body weight, animals treated with WCE did not lose weight as compared to control animals over the 8 week course of the experiment. See FIG. 4B. By contrast, docetaxel caused a large decrease in body weight due to the toxicity of this drug. Id. Importantly, mice treated with both WCE and docetaxel lost significantly less weight than animals treated with docetaxel alone. Id. This data, taken together, indicates that WCE can improve the efficacy of docetaxel against an AR-negative tumor while at the same time reducing the toxicity of docetaxel.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, a person skilled in the art can easily ascertain the essential characteristics of the present invention, and without departing from the spirit and scope thereof, can make various changes and modifications of the present invention to adapt it to various usages and conditions. Thus, other embodiments are also within the claims.

The invention claimed is:

1. A composition comprising a standardized *Wedelia chinensis* extract prepared by a method comprising:
   providing an ethanolic extract of *Wedelia chinensis*;
   acid-hydrolyzing the ethanolic extract;
   neutralizing the acid-treated ethanolic extract;
   applying the neutralized acid-treated ethanolic extract to a reverse phase column;
   eluting and collecting fractions from the reverse phase column;
   assaying in vitro the collected fractions for anti-androgen receptor activity; and
   combining fractions having the highest anti-androgen receptor activity amongst the collected fractions.

2. The composition of claim 1, wherein the eluting step is achieved with a water:ethanol gradient.

3. The composition of claim 2, wherein the water:ethanol gradient is from 80% water: 20% ethanol to 50% water: 50% ethanol by volume.

4. The composition of claim 3, wherein six fractions are collected.

5. The composition of claim 4, wherein in the combining step, two fractions having the highest anti-androgen receptor activity as compared to the anti-androgen receptor activity of each of the fractions are combined.

6. The composition of claim 1, wherein the anti-androgen receptor activity is determined by a prostate-specific antigen promoter/reporter assay.

7. The composition of claim 6, wherein the fractions having the highest anti-androgen receptor activity have an $IC_{50} \leq 300$ ng/ml in the promoter/reporter assay.

8. A method for treating an androgen-stimulated disorder in a subject, the method comprising identifying a subject in need of treatment for an androgen-stimulated disorder and administering to the subject in need thereof the composition of claim 1 in an amount effective for treating the androgen-stimulated disorder.

9. The method of claim 8, wherein the standardized *Wedelia chinensis* extract in the composition has been qualified prior to the administering step.

10. The method of claim 9, wherein the androgen-stimulated disorder is prostate cancer, benign prostate hypertrophy, breast cancer, male alopecia, *Propionibacterium acnes* infection, polycystic ovarian syndrome, autosomal dominant polycystic kidney disease, or hyperandrogenism.

11. The method of claim 10, wherein the prostate cancer is castration-resistant prostate cancer.

* * * * *